United States Patent [19]

Varma

[11] 4,252,733
[45] Feb. 24, 1981

[54] 17-SUBSTITUTED SULFONYL-16,16-DISUBSTITUTED ANDROSTENES

[75] Inventor: Ravi K. Varma, Belle Mead, N.J.

[73] Assignee: E. R. Squibb & Sons, Inc., Princeton, N.J.

[21] Appl. No.: 135,824

[22] Filed: Mar. 31, 1980

[51] Int. Cl.³ .............................................. C07J 1/00
[52] U.S. Cl. .............................................. 260/397.45
[58] Field of Search ............................ 260/397.45 LT

[56] References Cited

U.S. PATENT DOCUMENTS

| | | | |
|---|---|---|---|
| 4,091,036 | 5/1978 | Varma | 260/239.55 R |
| 4,094,840 | 6/1978 | Varma | 260/239.55 R |
| 4,133,811 | 1/1979 | Varma | 260/239.55 R |
| 4,146,538 | 3/1979 | Varma et al. | 260/239.55 R |
| 4,183,924 | 1/1980 | Green et al. | 260/397.45 |

Primary Examiner—Elbert L. Roberts
Attorney, Agent, or Firm—Lawrence S. Levinson; Donald J. Barrack

[57] ABSTRACT

Topical antiinflammatory activity is exhibited by steroids having the formula

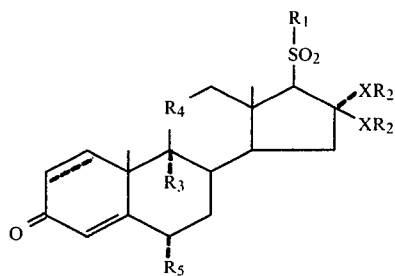

wherein
X is oxygen or sulfur;
$R_1$ is alkyl or aryl;
$R_2$ is alkyl or arylalkyl, or together the $R_2$ groups are —$(CH_2)_n$— wherein n is 2 or 3;
$R_3$ is hydrogen, fluoro, chloro, bromo or iodo;
$R_4$ is carbonyl or β-hydroxymethylene; and
$R_5$ is hydrogen, methyl or fluorine.

7 Claims, No Drawings

17-SUBSTITUTED SULFONYL-16,16-DISUBSTITUTED ANDROSTENES

BRIEF DESCRIPTION OF THE INVENTION

Steroids having the formula

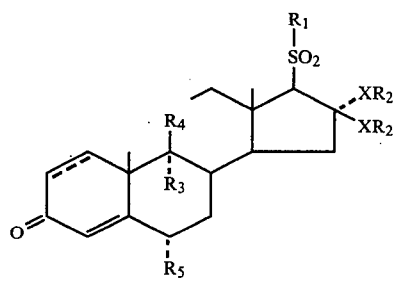

have topical antiinflammatory activity. In formula I, and throughout the specification, the symbols are as defined below:

X is oxygen or sulfur;

$R_1$ is alkyl or aryl;

$R_2$ is alkyl or arylalkyl, or together the $R_2$ groups are $-(CH_2)_n-$ wherein n is 2 or 3;

$R_3$ is hydrogen, fluoro, chloro, bromo or iodo;

$R_4$ is carbonyl or $\beta$-hydroxymethylene; and $R_5$ is hydrogen, methyl or fluorine.

A dotted line in the 1,2-position of a structural formula in this disclosure indicates the optional presence of ethylenic unsaturation.

The term "aryl," as used throughout the specification, whether by itself or as part of a larger group, refers to phenyl or phenyl substituted with one or two alkyl, alkoxy or halo groups.

The term "halo," as used throughout the specification, whether by itself or as part of a larger group, refers to fluoro, chloro, bromo or iodo (chloro and bromo are preferred).

The terms "alkyl" and "alkoxy", as used throughout the specification, whether individually or as part of a larger group, refer to groups having 1 to 10 carbon atoms.

DETAILED DESCRIPTION OF THE INVENTION

The steroids of formula I are physiologically active substances that possess glucocorticoid and antiinflammatory activity. They can be used topically in the treatment of skin conditions such as dermatitis, sunburn, neurodermatitis, eczema, and anogenital pruritus. The steroids of formula I can be used in the range of 0.01 to 5.0% by weight, preferably 0.05 to 2.0% by weight in a conventional cream or lotion.

The steroids of this invention can be prepared from the corresponding 16-halo-$\Delta^{4,16}$-steroid having the formula

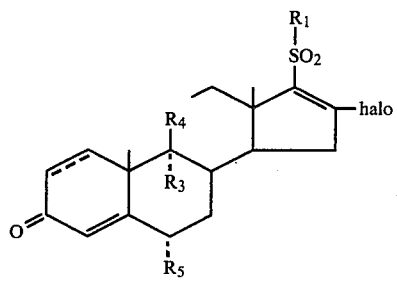

The preparation of the steroids of formula II is described in copending United States patent application Ser. No. 135,823, filed Mar. 31, 1980.

As disclosed therein, reaction of the appropriate androsten-17-one with a thiol compound having the formula $$R_1-SH \qquad (III)$$

in the presence of a Lewis acid (e.g., boron trifluoride etherate), yields an intermediate having the formula

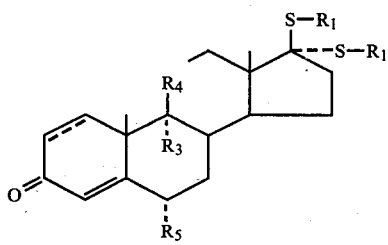

The reaction can be run in an organic solvent (e.g., a halogenated hydrocarbon), or a mixture of organic solvents. The use of some glacial acetic acid improves yields. Reaction conditions are not critical and the reaction can be convenient run at room temperature, preferably in an inert atmosphere (e.g., argon or nitrogen). Better yields may be obtained with relatively short reaction times (less than 1 hour).

An androstene of formula IV can be converted to the corresponding steroid having the formula

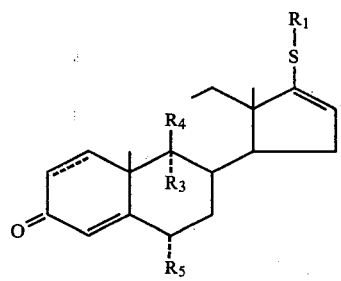

by simply heating the steroid in an inert solvent (e.g., diethylbenzene or dichlorobenzene).

Reaction of an androstene of formula V with an N-halosuccinimide, preferably in a halogenated hydrocarbon solvent, yields the corresponding steroid having the formula

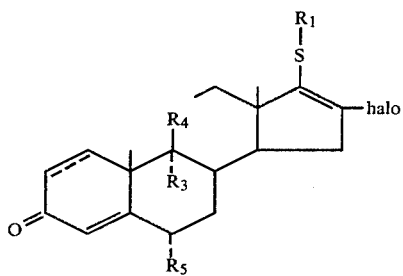

Oxidation of an androstene of formula VI with at least two equivalents of a peracid (e.g., m-chloroperbenzoic acid), a peracid salt (e.g., sodium m-periodate) or a peroxide (e.g., hydrogen peroxide) yields the corresponding sulfonyl steroid having the formula

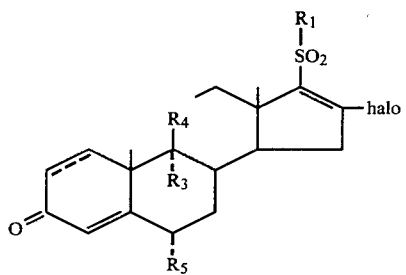

A steroid of formula VII can be reacted with an alcohol having the formula $R_2$—OH, a thiol having the formula $R_2$—SH, ethylene glycol, 1,3-propylene glycol, 1,2-ethanedithiol or 1,3-propanedithiol to obtain the products of formula I. The reaction is run in the presence of an alkali metal alkoxide or in the presence of a non-nucleophilic tertiary organic amine such as 1,5-diazobicyclo [5.4.0]undec-5-ene (often referred to as DBU).

Those steroids of formula I wherein $R_3$ is fluoro are preferred. Also preferred are those steroids of formula I wherein $R_4$ is $\beta$-hydroxymethylene. Particularly preferred are the steroids of this invention having the formula

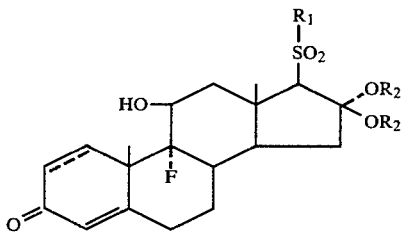

The following examples are specific embodiments of this invention.

EXAMPLE 1

(11$\beta$,17$\beta$)-17-(Ethylsulfonyl)-9-fluoro-11-hydroxy-16,16-dimethoxyandrosta-1,4-dien-3-one (A)

(11$\beta$)-16-Chloro-17-(ethylthio)-9fluoro-11-hydroxy-17-androsta-1,4,16-trien-3-one A solution of 1.5 g of (11$\beta$)-17-(ethylithio)-9-fluoro-11-hydroxyandrosta-1,4,16-trien-3-one in 70 ml of dry dichloromethane is stirred with 609 mg of N-chlorosuccinimide at room temperature under a nitrogen atmosphere for 2.5 hours. The resulting solution is diluted with 140 ml of chloroform. The chloroform solution is washed with saturated NaHCO$_3$ solution and water, dried over anhydrous Na$_2$SO$_4$ and evaporated in vacuo to give 1.65 g of a foam. The foam is dissolved in chloroform-hexane (4:1) and chromatographed on a 60 g-silica gel column. Elution with chloroform-hexane (4:1) gives 1.2 g of a tlc-homogeneous material. Crystallization from acetone-hexane gives 815 mg of an analytical specimen of the title compound, melting point 240°–241° C., dec.

Anal. calc'd for $C_{21}H_{26}ClFO_2S$: C,63.54; H,6.60; Cl,8.93; F,4.79; S,8.08, Found: C,63.42; H,6.37; Cl8.84; F,5.02; S,8.23.

(B)

(11$\beta$)-16-Chloro-17-(ethylsulfonyl)-9-fluoro-11-hydroxy-17-androsta-1,4,16-trien-3-one A solution of 2.3 g of (11$\beta$)-16-chloro-17-(ethylthio)-9-fluoro-11-hydroxy-17-androsta-1,4,16-trien-3-one and 2.35 g of m-chloroperoxybenzoic acid (85%) in 350 ml of dry dichloromethane is stirred at room temperature under a nitrogen atmosphere for 1 hour. The resulting solution is washed with water, saturated NaHCO$_3$ solution and water. The organic solution is dried over anhydrous Na$_2$SO$_4$ and evaporated in vacuo to give 2.45 g of tlc-homogenous title compound, melting point 270°–275° C., dec.

(C)

(11$\beta$,17$\beta$)-17-(Ethylsulfonyl)-9-fluoro-11-hydroxy-16,16-dimethoxyandrosta-1,4-dien-3-one To a homogenous solution of sodium (425 mg) in dry methanol (190 ml) is added 1.287 g of (11$\beta$)-16-chloro-17-(ethylsulfonyl)-9-fluoro-11-hydroxy-17-androsta-1,4,16-trien-3-one. The suspension is stirred at 70° C. (oil bath temperature) under a nitrogen atmosphere for 3 hours. The resulting solution is cooled and 2 ml of water is added. The solvent is partially removed in vacuo at room temperature and the resulting slurry is diluted with water and extracted with ethyl acetate. The aqueous solution is saturated with sodium chloride and extracted with ethyl acetate. The ethyl acetate solutions are combined, washed with water, dried over anhydrous Na$_2$SO$_4$ and evaporated in vacuo to give 1.2 g of a foam material. This was dissolved in 1:9 hexane-chloroform and chromatographed on a 60 g-silica gel column. Elution with chloroform-ethyl acetate (5:95, 1:9 and 1:4) gives 505 mg of (11$\beta$)-17-(ethylsulfonyl)-9-fluoro-11-hydroxy-16-methoxyandrosta-1,4,16-trien-3-one and 440 mg of mixture of that compound and (11$\beta$,17$\beta$)-(ethylsulfonyl)-9-fluoro-11hydroxy-16,16-dimethoxyandrosta-1,4-dien-3-one. The mixture is combined with a similar mixture from another run (giving a total of 645 mg) and dissolved in chloroform and chromatographed on precoated silica gel tlc plates (20 cm$\times$20 cm$\times$0.5 mm, 1:1 ethyl acetate-chloroform development) to give 370 mg of tlc-homogeneous product. Crystallization from acetone-hexane gives 315 mg of an analytical specimen of the title compound, melting point 268°–270° C.

Anal. calc'd for $C_{23}H_{33}FO_6S$: C,60.50; H,7.28; F,4.16; S7.02. Found: C,60.43; H,7.30; F,4.20; S,7.05.

EXAMPLES 2–6

Following the procedure of Example 1, but substituting the steroid listed in column I for (11β)-17-(ethylthio)-9-fluoro-11-hydroxyandrosta-1,4,16-trien-3-one in part A and the compound listed in column II for the methanol in part C, yields the steroid listed in column III.

| | Column I | Column II | Column III |
|---|---|---|---|
| 2. | (11β)-9-fluoro-11-hydroxy-17-(phenylthio)androsta-1,4,16-trien-3-one | ethylene glycol | (11β,17β)-16,16-ethylenedioxy-9-fluoro-17-(phenylsulfonyl)-11-hydroxyandrosta-1,4-dien-3-one |
| 3. | (11β)-17-(ethylthio) 9-fluoro-11-hydroxyandrosta-1,4,16-trien-3-one | 1,3-propylene glycl | (11β,17β)-17-ethylsulfonyl-9-fluoro-11-hydroxy-16,16-(propylenedioxylandrosta-1,4-dien-3-one |
| 4. | 9-fluoro-17-(methylthio)-androsta-1,4,16-trien-3,11-dione | benzyl alcohol | (17β)-16,16-di(phenylmethyl)-9-fluoro-17-(methylsulfonyl)androsta-1,4-dien-3,11-dione |
| 5. | (11β)-9-fluoro-11-hydroxy-17-(phenylthio)androsta-1,4,16-trien-3-one | 1,2-ethanedithiol | (11β,17β)-16,16-ethylenedithio-9-fluoro-11-hydroxy-17-(phenylsulfonyl)androsta-1,4-dien-3-one |
| 6. | (11β)-9-fluoro-11-hydroxy-17-(methylthio)androsta 4,16-dien-3-one | 1,3-propanedithiol | (11β,17β)-9-fluoro-11-hydroxy-17-(methylsulfonyl)-androst-4-en-3-one |

What is claimed is:
1. A steroid having the formula

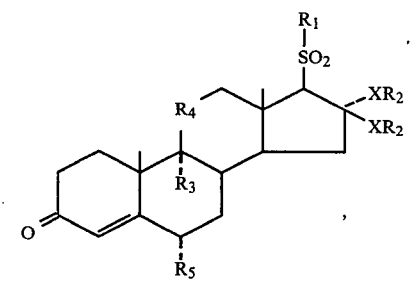

or the 1,2-dehydro derivative thereof, wherein
X is oxygen or sulfur;
$R_1$ is alkyl or aryl;
$R_2$ is alkyl or arylalkyl, or together the $R_2$ groups are $-(CH_2)_n-$ wherein n is 2 or 3;
$R_3$ is hydrogen, fluoro, chloro, bromo or iodo;
$R_4$ is carbonyl or β-hydroxymethylene;
$R_5$ is hydrogen, methyl or fluorine.

2. A steroid in accordance with claim 1 wherein X is oxygen.

3. A steroid in accordance with claim 2 wherein $R_2$ is methyl.

4. A steroid in accordance with claim 1 wherein $R_3$ is fluoro.

5. A steroid in accordance with claim 1 wherein $R_4$ is β-hydroxymethylene.

6. A steroid in accordance with claim 1 having the formula

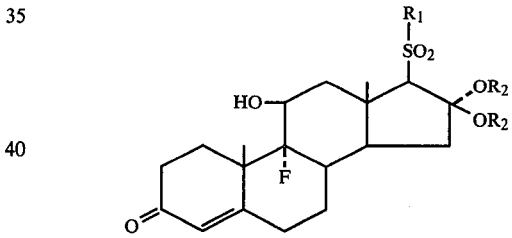

or the 1,2-dehydro derivative thereof.

7. The steroid in accordance with claim 6, (11β,17β)-17-(ethylsulfonyl)-9-fluoro-11-hydroxy-16,16-dimethoxyandrosta-1,4-dien-3-one.

* * * * *

UNITED STATES PATENT OFFICE
CERTIFICATE OF CORRECTION

Patent No. 4,252,733           Dated February 24, 1981

Inventor(s) Ravi K. Varma

It is certified that error appears in the above-identified patent and that said Letters Patent are hereby corrected as shown below:

Column 2, line 42 "convenient" should read --conveniently--
Column 3, line 63 insert a hyphen after "9"
Column 3, line 66 "(ethylithio)" should read --(ethylthio)--
Column 4, line 15 "Cl18.84" should read --Cl, 8.84--
Column 4, line 68 "S7.02" should read --S, 7.02--
Column 4, line 56 insert a hyphen after "11"
Column 4, line 68 "S7.02" should read --S, 7.02--
In the table, Column II, Item 3 "glycl" should read --glycol--
In the table, Column III, Item 3 "(propylenedioxylandrosta-" should read --(propylenedioxy)androsta--
In the table, Column III, Item 6 insert --16,16-(propylenedithio)-- before "androst"

Signed and Sealed this

Second Day of June 1981

[SEAL]

Attest:

RENE D. TEGTMEYER

Attesting Officer

Acting Commissioner of Patents and Trademarks